United States Patent [19]

Cheng

[11] 4,254,141

[45] Mar. 3, 1981

[54] INSECTICIDAL CARBAMOYL SULFIDES

[75] Inventor: Jiin-Duey Cheng, Wilmington, Del.

[73] Assignee: E. I. Du Pont de Nemours and Company, Wilmington, Del.

[21] Appl. No.: 139,836

[22] Filed: Apr. 24, 1980

Related U.S. Application Data

[63] Continuation-in-part of Ser. No. 18,293, Mar. 6, 1979.

[51] Int. Cl.³ .................. A01N 41/12; C07D 339/08; C07C 119/18; C07C 145/02
[52] U.S. Cl. .................................... 424/298; 424/277; 424/285; 424/320; 260/346.73; 260/453 RW; 542/416; 549/21

[58] Field of Search .................. 549/21; 260/543 RW, 260/551 S, 346.73; 424/277, 298, 320, 285; 542/416

[56] References Cited

U.S. PATENT DOCUMENTS

| | | | |
|---|---|---|---|
| 4,004,031 | 1/1977 | Drabek | 424/298 |
| 4,029,688 | 6/1977 | D'Silva | 424/298 |

*Primary Examiner*—Natalie Trousof
*Assistant Examiner*—L. Hendriksen

[57] ABSTRACT

Carbamoyl sulfides such as dimethyl N,N'-[2,3-butanediylidenebis[nitrilooxycarbonyl(N-methylimino)thio(N-methylimino)carbonyloxy]]bis[ethanimidothioate] useful for control of insects and nematodes.

45 Claims, No Drawings

INSECTICIDAL CARBAMOYL SULFIDES

CROSS REFERENCE TO RELATED APPLICATIONS

This application is a continuation-in-part of Ser. No. 018,293, filed Mar. 6, 1979.

BACKGROUND OF THE INVENTION

This invention relates to insecticidal and nematicidal carbamates.

Insecticidal carbamates are known in the prior art, e.g.

(a) Belgian BE No. 848,912 discloses pesticidal symmetrical bis-N-substituted carbamyl sulfides of the formula

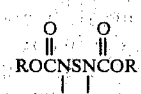

where R and R' represent substituents of varying scope;

(b) Belgian BE No. 848,913 discloses pesticidal unsymmetrical bis carbamyl sulfides of the formula

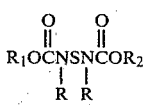

where R, $R_1$ and $R_2$ represent substituents of varying scope;

(c) German DT No. 2,813,281 discloses pesticidal bis-carbamoyl-oximino-disulfides of the formula

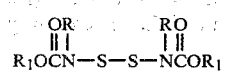

where R and $R_1$ represent substituents of varying scope.

SUMMARY OF THE INVENTION

This invention relates to novel compounds of Formula I, to agriculturally useful compositions of these compounds and to the method of use of these compounds as insecticides and nematicides.

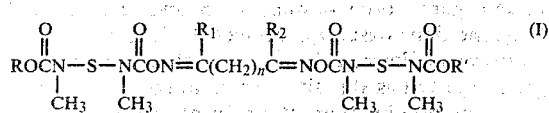 (I)

wherein
R and R' are independently

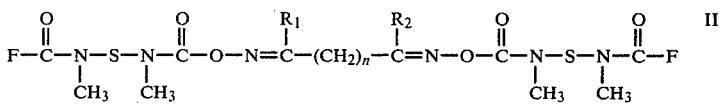

$R_1$ is hydrogen, $C_1$–$C_4$ alkyl, $C_5$–$C_6$ cycloalkyl, $C_1$–$C_3$ alkylthio, chlorine, chloromethyl, $$-\overset{O}{\overset{\|}{C}}N(CH_3)_2, R_5SCH_2-, -\overset{O}{\overset{\|}{C}}OR_6,$$

phenyl or phenyl substituted with $C_1$–$C_4$ alkyl;

$R_2$ is hydrogen, $C_1$–$C_4$ alkyl, $C_5$–$C_6$ cycloalkyl, chlorine, $C_1$–$C_3$ alkylthio, phenyl or phenyl substituted with $C_1$–$C_4$ alkyl;

$R_1$ and $R_2$ can be taken together to form a carbocyclic bridge of three to five carbon atoms, or a bridge of the formula $-SCH_2CH_2S-$;

$R_3$ is $C_1$–$C_3$ alkyl;
$R_4$ is $C_1$–$C_3$ alkyl;
$R_5$ is $C_1$–$C_3$ alkyl;
$R_6$ is $C_1$–$C_6$ alkyl; and n is 0, 1 or 2;
provided that n is 0 when
(1) $R_1$ is chloromethyl or $R_4SCH_2$, or
(2) $R_1$ and $R_2$ are taken together to form a carbocyclic bridge or a bridge of the formula $-SCH_2CH_2S-$, or
(3) at least one of $R_1$ and $R_2$ is alkylthio;
and provided that when n is 0, one of $R_1$ and $R_2$ cannot be H when the other is phenyl or phenyl substituted with $C_1$–$C_4$ alkyl; and further provided that when n is 1, $R_1$ and $R_2$ cannot both be t-butyl, phenyl, phenyl substituted with $C_1$–$C_4$ alkyl or combination thereof.

Also, this invention relates to novel intermediates of Formula II useful for preparation of compounds of Formula I $$\overset{O}{\overset{\|}{F-C}}-\underset{CH_3}{N}-S-\underset{CH_3}{N}-\overset{O}{\overset{\|}{C}}-O-N=\overset{R_1}{\underset{}{C}}-(CH_2)_n-\overset{R_2}{\underset{}{C}}=N-O-\overset{O}{\overset{\|}{C}}-\underset{CH_3}{N}-S-\underset{CH_3}{N}-\overset{O}{\overset{\|}{C}}-F \quad \text{II}$$

wherein $R_1$, $R_2$ and n are as previously defined.

DETAILED DESCRIPTION OF THE INVENTION

Preferred Compounds

Preferred for their high activity and/or favorable cost are compounds of Formula I wherein
(1) R and R' are identical; or
(2) $R_3$ is $CH_3$; or
(3) $R_1$ and $R_2$ are independently hydrogen, $C_1$–$C_4$ alkyl,

phenyl, phenyl substituted with $C_1$–$C_4$ alkyl, or where $R_1$ and $R_2$ are taken together to form a carbocyclic bridge of three to five carbon atoms, or (4) n is O.

More preferred for their higher activity and/or more favorable cost are the preferred compounds of Formula I wherein
R and R' are

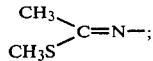

$R_1$ and $R_2$ are independently hydrogen or $C_1$–$C_4$ alkyl; and n is O; provided at least one of $R_1$ and $R_2$ is other than hydrogen.

Specifically preferred for their excellent activity and/or most favorable cost are dimethyl N,N'-[2,3-butanediylidenebis[nitrilooxycarbonyl(N-methylimino)thio(N-methylimino)carbonyloxy]]bis[ethanimidothioate]

dimethyl N,N'-[1,2-propanediylidenebis[nitrilooxycarbonyl(N-methylimino)thio(N-methylimino)carbonyloxy]]bis[ethanimidothioate]

dimethyl N,N'-[2,4-pentanediylidenebis[nitrilooxycarbonyl (N-methylimino)thio(N-methylimino)carbonyloxy]]bis[ethanimidothioate]

dimethyl N,N'-[2,5-hexanediylidenebis[nitrilooxycarbonyl (N-methylimino)thio(N-methylimino)carbonyloxy]]bis[ethanimidothioate]

N-methyl-N-[N-methyl-N-(2-methyl-2-methylthio-propylideneaminooxycarbonyl)aminothio]carbamic acid, diester with 2,3-butanedione, dioxime N,N'-[2,3-butanediylidenebis[nitrilooxycarbonyl(N-methylaminothio-(N-methylamino)carbonyloxy]-bis]-2-(dimethylamino)-2-oxoethanimidothioic acid, dimethyl ester:

SYNTHESIS The novel compounds of Formula I in which R and R' are identical can be prepared by the reaction shown in Equation A.

tem such as toluene-water, methylene chloride-water mixture and the like in the presence of a quaternary ammonium or phosphonium salt as a phase transfer catalyst at $-15°$ C. to $60°$ C. An equivalent or a slight excess of metal hydroxide can be used as acid scavenger. It is preferred that the reaction be conducted at $10°$ C. to $30°$ C. by using sodium hydroxide or potassium hydroxide as acid acceptor in the presence of 10 to 30 mole percent of phase transfer catalyst such as cetyltrimethylammonium bromide or benzyltrimethylammonium hydroxide.

The reaction can also be carried out in the absence of acid acceptor by directly reacting the carbamyl fluoride of Formula II with a dianion of Formula III in an aprotic solvent such as tetrahydrofuran, toluene, acetonitrile, methylene chloride and the like at temperatures between $-50°$ and $40°$ C., preferably, at $-30°$ to $25°$ C. The dianion of Formula III is preferably generated in situ by reaction of the dioxime III with a metal hydride or metal amide in a proper solvent.

An alternate method to prepare the compounds of Formula I is shown by Equation B.

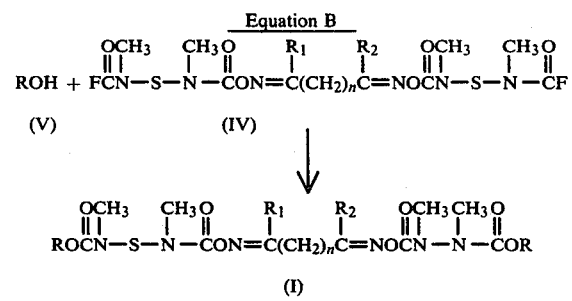

wherein R, $R_1$, $R_2$ and n are as previously defined.

The compounds of Formula I (R=R') can be obtained by treatment of the bis-carbamyl fluoride of For-

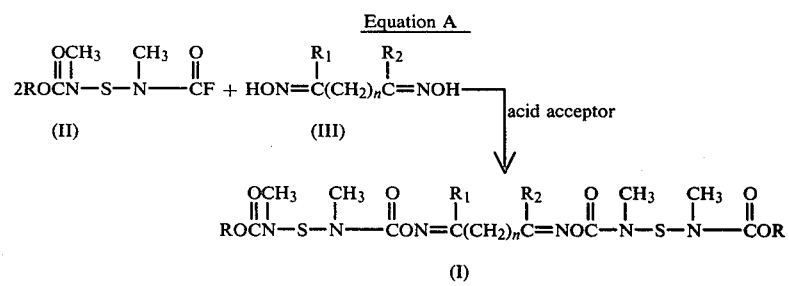

wherein R, $R_1$, $R_2$ and n are as previously defined.

The reaction can be carried out in an inert solvent such as acetonitrile, tetrahydrofuran, toluene, xylene, methylene chloride, chloroform and the like at temperatures between $-20°$ and $80°$ C., preferably, at $-5°$ to $40°$ C. The acid acceptor used in this reaction can be an organic tertiary amine such as triethylamine, N,N-dimethylaniline, pyridine, and the like.

The reaction of a dioxime (III) and the carbamoyl fluoride (II) can be carried out in a heterogeneous sysmula IV with either the metal salt of an oxime of Formula V or the oxime of Formula V itself in the presence of an organic tertiary amine as an acid acceptor under the conditions described previously. The metal salt of an oxime of Formula V as previously described can be generated and used in situ by reaction of the oxime with metal hydride in an aprotic solvent, e.g. tetrahydrofuran, toluene, acetonitrile, etc., at $-5°$ to $20°$ C.

Compounds of Formula I where R and R' are different can be conveniently prepared as Equation C.

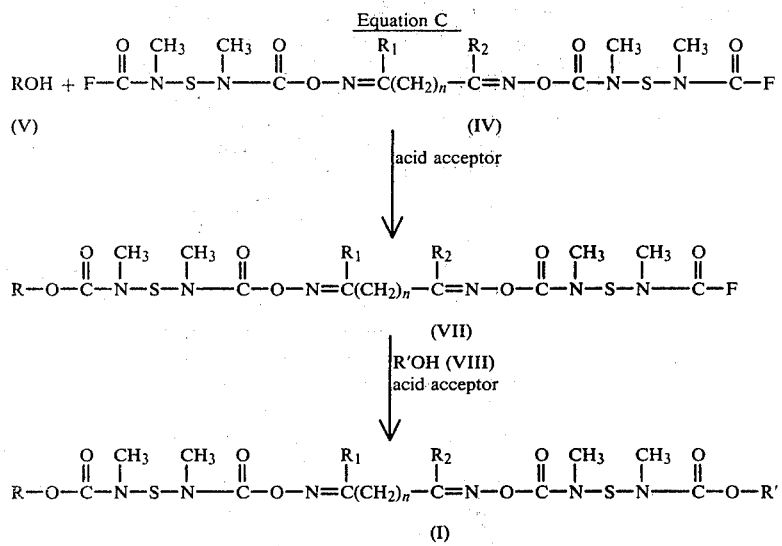

The intermediate VII can be prepared preferably by mixing an equivalent of an oxime V, bis-carbamoyl fluoride IV and an acid acceptor such as triethylamine at −15° C. to 40° C. in an inert solvent such as chloroform. Under similar reaction conditions, the subsequent reaction of the compound of Formula VII with another oxime VIII in the presence of, for example, triethylamine, would give the product of Formula I (R≠R').

Required intermediates of Formula IV can be prepared by the reaction as given in Equation D.

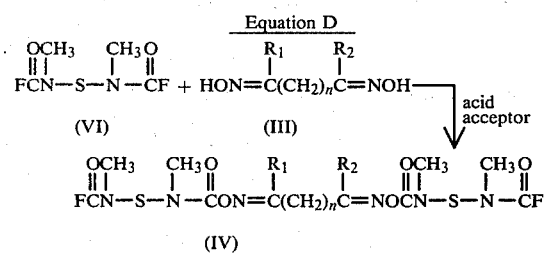

The reaction shown in Equation D can be carried out in an inert solvent such as toluene, xylene, tetrahydrofuran, acetonitrile, methylene chloride at temperatures between −20° and 80° C., preferably, at −5° to 40° C. An organic tertiary amine such as triethylamine, N,N-dimethylaniline, or pyridine, or an inorganic metal bicarbonate or carbonate can be used as an acid acceptor.

The carbamyl fluoride of Formula II and bis(N-methyl-N-fluorocarbonylamino)sulfide (VI) can be prepared by the methods taught in DT No. 2,654,282.

In the above reaction procedures, pressure is not critical, but, for convenience, atmospheric pressure is preferred.

The preparation of compounds of Formula I can be more clearly illustrated by the following examples. All temperatures are in degrees centigrade and all percentages are by weight unless otherwise stated.

EXAMPLE 1

Dimethyl
N,N'-[2,3-butanediylidenebis[nitrilooxycarbonyl
(N-methylimino)thio(N-methylimino)carbonyloxy]]-
bis[ethanimidothioate]

Two grams of dimethylglyoxime disodium salt octahydrate was added in portions to a solution of 3.7 g of 0-[N-methyl-N-(N'-methyl-N'-fluorocarbonylaminosulfenyl)carbamoyl]-1-methylthioacetaldoxime in 30 ml of dry tetrahydrofuran (THF) at temperatures below −20° C. The mixture was stirred on an ice bath for 3 hours after the addition. Then ether and water were added into the reaction mixture. The precipitate was collected by filtration, washed with water, acetone and air-dried to give 2.6 g of dimethyl N,N'-[2,3-butanediylidenebis[nitrilooxycarbonyl(N-methylimino)thio(N-methylimino)carbonyloxy]]bis[ethanimidothioate], m.p. 204°–206° C.

Alternatively, a solution of 5.5 g of O-[N-methyl-N-(N'-fluorocarbonylaminosulfenyl)carbamoyl]-1-methylthioacetaldoxime in a mixture of 40 ml of toluene and 20 ml of tetrahydrofuran was added dropwise in 5 min. to a mixture of 3 g of dimethylglyoxime disodium salt octahydrate and 1 g of cetyltrimethylammonium bromide in 50 ml of water at 15° C. to 20° C. with vigorous stirring.

After stirring at room temperature for 30 minutes, the solid was collected by filtration, washed with water, toluene, and air-dried to give 2.6 g of dimethyl N,N'-[2,3-butanediylidenebis[nitrolooxycarbonyl (N-methylimino)thio(N-methylimino)carbonyloxy]]-bis[ethanimidothioate].

EXAMPLE 2

Dimethyl
N,N'-[1,2-propanediylidenebis[nitrilooxycarbonyl
(N-methylimino)thio(N-methylimino)carbonyloxy]]bis-
[ethanimidothioate]

In a flask was charged 1 g of 50% of sodium hydride dispersed in mineral oil. Mineral oil was removed by washing the hydride with dry hexane under a nitrogen atmosphere, and the hexane solution was decanted. Then 20 ml. of dry THF was added. To the suspension 0.9 g of methylglyoxime was added in portions at temperatures below 20° C. After stirring for 1 hour, a solution of 5 g of 0-[N-methyl-N-(N'-methyl-N'-fluorocarbonylaminosulfenyl)carbamoyl)-1-methylthioacetadoxime in 30 ml. of dry THF was added rapidly at −20° to −30° C. The mixture was stirred on an ice bath for an hour. Then ether was added. The excess of sodium hydride was quenched by careful addition of water. The precipitate was collected by filtration, washed with water, then hexane, and was air-dried to give 2.5 g of dimethyl N,N'-[1,2-propanediylidenebis[nitrilooxycarbonyl(N-methylimino)thio(N-methylimino)carbonyloxy]]-bis[ethanimidothioate], m.p. 175°–178° C. (dec.).

EXAMPLE 3

Dimethyl N,N'-[ethanediylidenebis[nitrilooxycarbonyl-(N-methylimino)thio(N-methylimino)carbonyloxy]]bis-[ethanimidothioate]

A solution of 1.5 g of triethylamine in 10 ml. of dry acetonitrile was added dropwise to a mixture of 0.6 g. of glyoxime and 3.9 g of 0-[N-methyl-N-(N'-methyl-N'-fluorocarbonylaminosulfenyl)carbamoyl]-1-methylthioacetaldoxime in 30 ml. of dry acetonitrile on an ice bath with stirring. The mixture was allowed to warm up slowly and stirred at ambient temperature. for 17 hours. The precipitate was collected by filtration, washed with water, acetonitrile and air-dried to give 1 g of dimethyl N,N'-[ethanediylidenebis[nitrilooxycarbonyl(N-methylimino)thio[N-methylimino)carbonyloxy]]bis[ethanimidothioate], m.p. 167°–168.5° C. (dec.).

EXAMPLE 4

N,N'-[2,3-butanediylidenebis[nitrilooxycarbonyl (N-methylimino)thio]bis[N-methylcarbamic fluoride]

A solution of 4.1 g of triethylamine in 10 ml of dry acetonitrile was added dropwise to a mixture of 2.3 g of dimethylglyoxime and 7.4 g of bis(N-methyl-N-fluorocarbonylamino)sulfide in 40 ml of dry acetonitrile at 0° to 5° C. The mixture was stirred on an ice bath for 30 minutes and at ambient temperature for 3 hours. To the suspension, water and ether were added. The precipitate was collected by filtration, washed with water, a mixture of ether and n-chlorobutane, and air-dried to give 6 g of N,N'-[2,3-butanediylidenebis[nitrilooxycarbonyl (N-methylimino)thio]bis[N-methylcarbamic fluoride], m.p. 212°–215° C. (dec.).

EXAMPLE 5

Methyl N-[N-[N-[N-[1,2-dimethyl-2[[N-methyl-N-[N-methyl-N-[[1-(methylthio)ethylidene]aminooxycarbonyl]-aminothio]amino]carbonyloxyimino]ethylidene]aminooxycarbonyl]-N-methylaminothio]-N-methylaminocarbonyloxy]-2-(dimethylamino)-2-oxoethanimidothioate A solution of 1.1 g of triethylamine in 10 ml of methylene chloride was added dropwise to a suspension of 4.5 of N,N'-[2,3-butanediylidene-bis[nitrilooxycarbonyl(N-methylimino)thio]]bis [N-methylcarbamic fluoride] and 1.1 g of methyl N-hydroxyethanimidothioate in 90 ml of methylene chloride at 0° to 5° in 30 minutes. The mixture was stirred on an ice bath 3 hours. The unreacted starting material was separated by filtration. The filtrate was washed with three 80 ml portions of water and the organic layer was dried over anhydrous magnesium sulfate. The mixture was filtered and the filtrate was evaporated to give an oil, which was triturated with ether and methylene chloride mixture to give 3.1 g of methyl N-[N-[N-[2-[[N- [N-(fluorocarbonyl)-N-methylaminothio]-N-methylamino]-carbonyloxyimino]-1,2-dimethylethylidene]aminooxycarbonyl]-N-methylaminothio]-N-methylaminocarbonyloxy]ethanimidothioate.

IR (Nujol): 5.6μ, 5.7μ

NMR (CDCl$_3$) δ2.13, 2.33 and 2.40 (3S, 12H), 3.4 and 3.47 (2S, 12H).

This crude carbamic fluoride was used in the next reaction without further purification.

A solution of 1 g of triethylamine in 10 ml of methylene chloride was added dropwise to a solution of 3 g of the crude carbamic fluoride and 1.1 g of methyl 2-(dimethylamino)-N-hydroxy-2-oxoethanimidothioate in 50 ml of methylene chloride at 10° to 20° C. and stirred at room temperature for 2.5 hours. The solution was washed with three 50 ml portions of water, and the organic layer was dried over anhydrous magnesium sulfate. The mixture was filtered, and the filtrate was evaporated. Ether was added to the crude product followed by dilution with methylene chloride until the mass could flow freely. The solid was separated by filtration to give a mixture. The mother liquor was concentrated and diluted with ethers to give 0.5 g of the title compound, m.p. 87°–110° C. (glass).

IR (Nujol): 5.75μ, and 6.08μ

NMR (CDCl$_3$): δ2.3, 2.33 and 2.4 (3S, 15H), 3.02 and 3.08 (2S, 6H), 3.42 and 3.48 (2S, 12H).

Active compounds of Formula I that can be prepared according to the procedures demonstrated by the given examples are given, but not restricted, as follows:

TABLE 1

$$R_3C=NOC(O)N(CH_3)SN(CH_3)—CON=C(R_1)(CH_2)_nC(R_2)=NOC(O)N(CH_3)SN(CH_3)—CON=CR_3$$
$$|\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad|$$
$$R_4S \quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad SR_4$$

| $R_3$ | $R_4$ | $R_1$ | $R_2$ | n | melting point °C. |
|---|---|---|---|---|---|
| CH$_3$ | CH$_3$ | CH$_3$ | CH$_3$ | 1 | 131–140 (dec.) |
| CH$_3$ | CH$_3$ | C$_6$H$_5$ | C$_6$H$_5$ | 0 | 214–216.5 (dec.) |
| CH$_3$ | CH$_3$ | O=CN(CH$_3$)$_2$ | CH$_3$ | 0 | 184–189 (dec.) |
| CH$_3$ | CH$_3$ | CH$_3$ | CH$_3$ | 2 | 178–188 |
| CH$_3$ | CH$_3$ | Cl | Cl | 0 | 96–99.5 |
| CH$_3$ | CH$_3$ | CH$_3$S | CH$_3$S | 0 | 200–202.5 (dec.) |
| CH$_3$ | CH$_3$ | CO$_2$CH$_3$ | CH$_3$ | 0 | 173–176.5 (dec.) |
| CH$_3$ | CH$_3$ | CO$_2$(n-C$_6$H$_{13}$) | CH$_3$ | 0 | |
| CH$_3$ | CH$_3$ |  |  | 0 | |

TABLE 1-continued $$R_3C=NOC(O)N(CH_3)SN(CH_3)-CON=C(R_1)(CH_2)_nC(R_2)=NOC(O)N(CH_3)SN(CH_3)-CON=CR_3$$
with $R_4S$ and $SR_4$ substituents

| R₃ | R₄ | R₁ | R₂ | n | melting point °C. |
|---|---|---|---|---|---|
| CH₃ | CH₃ | n-C₃H₇S | n-C₃H₇S | 0 | 180–183.5 (dec.) |
| CH₃ | CH₃ | CH₃SCH₂ | CH₃ | 0 | oil |
| CH₃ | CH₃ | n-C₃H₇SCH₂ | CH₃ | 0 | 100–115 (dec.) |
| CH₃ | CH₃ | ClCH₂ | CH₃ | 0 | 166–168.5 (dec.) |
| CH₃ | CH₃ | n-C₄H₉ | n-C₄H₉ | 0 | |
| CH₃ | CH₃ | t-Bu-C₆H₄- | t-Bu-C₆H₄- | 0 | |
| CH₃ | CH₃ | —CH₂CH₂CH₂CH₂CH₂— | | 0 | |
| CH₃ | CH₃ | t-Bu | CH₃S | 0 | |
| CH₃ | CH₃ | t-Bu | H | 0 | |
| CH₃ | CH₃ | —CH₂CH₂CH₂CH₂— | | 0 | 170–173 (dec.) |
| CH₃ | CH₃ | —CH₂CH₂CH₂— | | 0 | |
| CH₃ | CH₃ | i-Pr-C₆H₄- | i-Pr-C₆H₄- | 0 | |
| CH₃ | CH₃ | CH₃-C₆H₄- | CH₃-C₆H₄- | 0 | |
| CH₃ | CH₃ | cyclopentyl | cyclopentyl | 0 | |
| CH₃ | CH₃ | CH₃CH₂ | CH₃CH₂ | 0 | |
| CH₃ | CH₃ | CH₃CH₂CH₂ | CH₃CH₂CH₂ | 0 | |
| CH₃ | CH₃ | (CH₃)₂CH | (CH₃)₂CH | 0 | |
| CH₃ | CH₃ | CH₃CH₂SCH₂ | CH₃ | 0 | |
| CH₃ | CH₃ | CH₃CH₂S | CH₃CH₂S | 0 | |
| CH₃ | CH₃ | C₆H₅ | CH₃ | 0 | 167–170 (dec.) |
| CH₃ | CH₃ | CH₃ | CH₃S | 0 | |
| CH₃ | CH₃ | —SCH₂CH₂S— | | 0 | 204–207 (dec.) |
| CH₃ | CH₃ | CH₃ | CH₃CH₂ | 0 | 193–195.5 (dec.) |
| C₂H₅ | CH₃ | CH₃ | CH₃ | 0 | |
| CH₃ | n-C₃H₇ | CH₃ | CH₃ | 0 | |
| n-C₃H₇ | CH₃ | CH₃ | CH₃ | 0 | |
| CH₃ | CH₃ | CH₃ | CH₃(CH₂)₃ | 0 | 99–104 |

TABLE 2

$$R-O-C(O)-N(CH_3)-S-N(CH_3)-CON=C(R_1)(CH_2)_n-C(R_2)=N-O-C(O)-N(CH_3)-S-N(CH_3)-C(O)-O-R'$$

| R | R' | R₁ | R₂ | n | melting point °C. |
|---|---|---|---|---|---|
| Me₂NC(O)-C(SCH₃)=N- | Me₂NC(O)-C(SCH₃)=N- | CH₃ | CH₃ | 0 | 185–188 (dec.) |
| Me₂NC(O)-C(SCH₃)=N- | Me₂NC(O)-C(SCH₃)=N- | CH₃ | CO₂CH₃ | 0 | |
| Me₂NC(O)-C(SCH₃)=N- | Me₂NC(O)-C(SCH₃)=N- | CH₃S | CH₃S | 0 | |
| Me₂NC(O)-C(SCH₃)=N- | Me₂NC(O)-C(SCH₃)=N- | CH₃CH₂ | CH₃CH₂ | 0 | |
| Me₂NC(O)-C(SCH₃)=N- | Me₂NC(O)-C(SCH₃)=N- | CH₃(CH₂)₃— | CH₃ | 0 | |
| Me₂NC(O)-C(SCH₂CH₃)=N- | Me₂NC(O)-C(SCH₂CH₃)=N- | CH₃ | CH₃ | 0 | |
| Me₂NC(O)-C(S-n-C₃H₇)=N- | Me₂NC(O)-C(S-n-C₃H₇)=N- | CH₃ | CH₃ | 0 | |

TABLE 2-continued $$R-O-\overset{O}{\underset{\|}{C}}-\overset{CH_3}{\underset{|}{N}}-S-\overset{CH_3}{\underset{|}{N}}-\overset{O}{\underset{\|}{C}}ON=\overset{R_1}{\underset{|}{C}}(CH_2)_n-\overset{R_2}{\underset{|}{C}}=N-O-\overset{O}{\underset{\|}{C}}-\overset{CH_3}{\underset{|}{N}}-S-\overset{CH_3}{\underset{|}{N}}-\overset{O}{\underset{\|}{C}}-O-R'$$

| R | R' | $R_1$ | $R_2$ | n | melting point °C |
|---|---|---|---|---|---|
| $CH_3SC(CH_3)_2CH=N$ | $CH_3SC(CH_3)_2CH=N$ | $CH_3$ | $CH_3$ | 0 | 117–118.5 |
| $CH_3SC(CH_3)_2CH=N$ | $CH_3SC(CH_3)_2CH=N$ | $CH_3CH_2$ | $CH_3CH_2$ | 0 | |
| $CH_3SC(CH_3)_2CH=N$ | $(CH_3)(CH_3S)C=N-$ | $CH_3$ | $CH_3$ | 0 | |
| $CH_3SC(CH_3)_2CH=N-$ | $Me_2NC(O)C(CH_3S)=N$ | $CH_3$ | $CH_3$ | 0 | |
| (2-isopropylidenedioxyphenyl) | (2-isopropylidenedioxyphenyl) | $CH_3$ | $CH_3$ | 0 | 155–161 (dec.) |
| (2-isopropylidenedioxyphenyl) | $(CH_3)(CH_3S)C=N-$ | $CH_3$ | $CH_3$ | 0 | |
| (2-isopropylidenedioxyphenyl) | $Me_2NC(O)C(CH_3S)=N-$ | $CH_3$ | $CH_3$ | 0 | |
| (2-isopropylidenedioxyphenyl) | $CH_3SC(CH_3)_2CH=N-$ | $CH_3$ | $CH_3$ | 0 | |
| $(CH_3)(CH_3CH_2S)C=N$ | $CH_3SC(CH_3)_2CH=N$ | $CH_3$ | $CH_3$ | 0 | |
| $(CH_3)(CH_3CH_2S)C=N$ | $Me_2NC(O)C(CH_3S)=N$ | $CH_3$ | $CH_3$ | 0 | |
| $CH_3SC(CH_3)_2CH=N$ | $CH_3SC(CH_3)_2CH=N$ | $C_6H_5$ | $C_6H_5$ | 0 | |

FORMULATION

Useful formulations of the compounds of Formula I can be prepared in conventional ways. They include dusts, granules, pellets, solutions, wettable powders, and the like. Many of these may be applied directly. Sprayable formulations can be extended in suitable media and used at spray volumes of from a few pints to several hundred gallons per acre. High strength compositions are primarily used as intermediates for further formulations. The formulations, broadly, contain about 1% to 99% by weight of active ingredient(s) and at least one of a) about 0.1% to 20% surfactant(s) and b) about 1% to 99% solid or liquid diluent(s). More specifically, they will contain these ingredients in the following approximate proportions:

TABLE 3

| | Active Ingredient | Diluent(s) | Surfactant(s) |
|---|---|---|---|
| Wettable Powders | 20–90 | 0–74 | 1–10 |
| Oil Suspensions, Solutions | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Dilutents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferable stable against phase separation at 0° C. McCutcheon's "Detergents and Emulsifiers Annual", MC Publishing Co., Ridgewood, NJ., as well as Sisely and Wood, "Encyclopedia of Surface Active Agents", Chemical Publ. Co., Inc., New York, 1964, list surfactants and recommended uses. All formulations can contain minor amounts of additives to reduce foam, caking corrosion, microbiological growth, etc. Preferably, ingredients should be approved by the U.S. Environmental Protection Agency for the use intended.

The method of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granule carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, N.Y., 1963, pp. 8-59ff.

For further information regarding the art of formulation see for example:

J. B. Buchanan, U.S. Pat. No. 3,576,834, Apr. 27, 1971, Col. 5, lines 36 through Col. 7, Line 70 and Ex. 1-4, 17, 106, 123-140;

R. R. Shaffer, U.S. Pat. No. 3,560,616, Feb. 2, 1971, Col. 3, Line 48 through Col. 7, line 26 and Ex. 3-9, 11-18;

E. Somers, "Formulation", Chapter 6 in Torgeson, "Fungicides", Vol. I, Academic Press, New York, 1967.

EXAMPLE 6

| Wettable Powder | |
| --- | --- |
| Dimethyl N,N'-[2,3-butanediylidenebis-[nitrilooxycarbonyl (N-methylimino)-thio (N-methylimino)carbonyloxy]]bis-[ethanimidothioate] | 30% |
| Dicotyl sodium sulfosuccinate | 1.5% |
| Sodium ligninsulfonate | 3% |
| Low viscosity methyl cellulose | 1.5% |
| Attapulgite | 64% |

The ingredients are thoroughly blended, passed through an air mill to produce an average particle size under 15 microns, reblended, and sifted through a U.S.S. No. 50 sieve (0.3 mm opening) before packaging.

All compounds of the invention may be formulated in the same manner.

EXAMPLE 7

| Wettable Powder | |
| --- | --- |
| Dimethyl N,N'-[1,2-propanediylidenebis-[nitrilooxycarbonyl (N-methylimino)-thio (N-methylimino)carbonyloxy]]bis-[ethanimidothioate] | 50% |
| Sodium alkylnaphthalenesulfonate | 2% |
| Low viscosity methyl cellulose | 2% |
| Diatomaceous earth | 46% |

The ingredients are blended, coarsely hammer-milled and then air milled to produce particles of active essentially all below 10 microns in diameter. The product is reblended before packaging.

EXAMPLE 8

| Dust | |
| --- | --- |
| Wettable powder of Example 7 | 10% |
| Pyrophyllite (powder) | 90% |

The wettable powder and the pyrophyllite diluent are thoroughly blended and then packaged. The product is suitable for use as a dust.

EXAMPLE 9

| Solution | |
| --- | --- |
| Dimethyl N,N'-[2,4-pentanediylidenebis-[nitrilooxycarbonyl (N-methylimino)-thio(N-methylimino)carbonyloxy]]bis-[ethanimidothioate] | 30% |
| Dimethylformamide | 70% |

The ingredients are combined and stirred to produce a solution, which can be used for low volume applications.

| Granule | |
| --- | --- |
| Wettable powder of Example 6 | 15% |
| Gypsum | 69% |
| Potassium sulfate | 16% |

The ingredients are blended in a rotating mixer and water sprayed on to accomplished granulation. When most of the material has reached the desired range of 1.0 to 0.42 mm. (U.S.S. No. 18 to 40 sieves), the granules are removed, dried, and screened. Oversize material is crushed to produce additional material in the desired range. These granules contain 4.5% active igredient.

EXAMPLE 11

| Extruded Pellet | |
| --- | --- |
| Dimethyl N,N'-[2,5-hexanediylidenebis-[nitrilooxycarbonyl(N-methylimino)-thio(N-methylimino)carbonyloxy]]bis-[ethanimidothioate] | 25% |
| Anhydrous sodium sulfate | 10% |
| Crude calcium ligninsulfonate | 5% |
| Sodium alkylnaphthalenesulfonate | 1% |
| Calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm opening). The granules held on a U.S.S. No. 40 sieve (0.42 mm opening) may be packaged for use and the fines recycled.

EXAMPLE 12

| Aqueous Suspension | |
|---|---|
| Dimethyl N,N'-[2,3-butanediylidenebis-[nitrilooxycarbonyl(N-methylimino)-thio(N-methylimino)carbonyloxy]]bis-[ethanimidothioate] | 25% |
| Hydrated attapulgite | 3% |
| Crude calcium ligninsulfonate | 10% |
| Sodium dihydrogen phosphate | 0.5% |
| Water | 61.5% |

The ingredients are ground together in a ball or roller mill until the solid particles have been reduced to diameters under 10 microns.

USE

The compounds of this invention of Formula I are useful for the control of arthropods and nematodes which are detrimental to agricultural, animals important to man, forestry, horticulture, the household, man-made structures, public health and stored products.

As demonstrated in the following examples, the compounds have provided a high degree of control of important pests with minimization of side effects known in prior art compounds such as phytotoxicity.

The compounds readily control pestiferous arthropods belonging to such orders as Acari, Lepidoptera, Humenoptera, Isoptera, Coleoptera, and Diptera. More specifically, arthropods controlled by the compounds of this invention include, but are not limited to, southern armyworm (*Spodoptera eridanis*), fall armyworm (*Spodoptera frugiperda*), soybean looper (*Pseudoplusia includens*), Mexican bean beetle (*Edplachna varivestis*), the housefly (*Musca domestica*), tobacco budworm (*Heliothis virescens*), bollworm (*Heliothis zea*), eastern tent caterpillar (*Malacosoma americanum*), brown dog tick (*Rhipicephalus sanguineus*), and black carpenter ant (*Camponotus pennsylvanicus*).

These compounds readily control pestiferous nematodes. More specifically, nematodes controlled by compounds of this invention include, but are not limited to, the root-knot nematode, *Meloidogyne incognita;* lesion nematode, *Pratylenchus* spp. and dagger nematode, Xiphinima.

The insects are controlled by applying one or more of the compounds to the locus of infestation, to the area to be protected, or to the pests themselves. For the control of insects on agricultural crops, compounds of this invention are generally applied to the foliage or other plant parts which are infested or which are to be protected. Effective amounts to be applied depend upon the specific compound used, the species to be controlled, its life stage, its size and location, the amount of rainfall, the time of year, moisture, temperature, type of application plant spacing, and other variables. In general, 0.05 to 10.0 kg/ha may be required for insect control in agriculture with rates of 0.15 to 5.0 kg/ha usually being sufficient in many situations. In large scale field operations, rates in the range of 0.25 to 3.0 kg/ha are generally used.

For the control of pestiferous arthropods of animals important to man, the household, man-made structures and stored products, compounds of this invention of formula I are generally applied to the item(s) which are infested or which are to be protected. Effective amounts to be applied depend upon the specific compound used, the species to be controlled, its life stage, its size and location, the amount of rainfall, the time of year, moisture, temperature, type of application and other variables. In general, 0.001% to 10% (by weight) preferably 0.05 to 5% and more preferably 0.01 to 2.5% of the compound of this invention will be applied in a composition such as in the form of a solution dispersion or dust.

Nematodes are controlled by applying the compounds to the locus of infestation, to the area to be protected or to the pest themselves. For the control of nematodes in agricultural crops, a compound of this invention is generally applied to a portion of the plant or surrounding soil which is infested or which is to be protected. Effective amounts to be applied depend upon the species to be controlled, its life stage, its size and location, the amount of rainfall, the time of year, moisture, temperature, soil type, percentage of area treated, type of application, and other variables. In general, 3 to 30 kg/ha may be required for nematode control in agriculture with rates of 5 to 10 kg/ha usually being sufficient in many situations.

The compounds of this invention of formula I possess significant advantages over prior art compounds. For example, their improved residual insecticidal activity can reduce the need for closely spaced multiple sprays resulting in greater economy to the grower and dissemination of less insecticide in the environment. An additional advantage is the reduced side-effects on cotton. Treated leaves remain green and free of reddening.

The compounds of this invention of formula I can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

FUNGICIDES methyl 2-benzimidazolecarbamate (carbendazim),
tetramethyl thiuram disulfide (thiram),
n-dodecylguanidine acetate (dodine),
manganese ethylenebisdithiocarbamate (maneb),
1,4-dichloro-2,5-dimethoxybenzene (chloroneb),
methyl 1-(butylcarbamoyl)-2-benzimidazolecarbamate (benomyl),
2-cyano-N-ethylcarbamoyl-2-methoxyimino acetamide (cymoxamide),
N-trichloromethylthiotetrahydrophthalimide (captan),
N-trichloromethylthiophthalimide (folpet);

BACTERICIDES tribasic copper sulfate,
streptomycin sulfate

ACARICIDES senecioic acid, ester with 2-sec-butyl-4,6-dinitrophenyl (Morocide ®),
6-methyl-1,3-dithiolo[2,3-B]quinoolin-2-one (Morestan ®), ethyl 4,4'(p-chlorophenyl)-2,2,2-trichloroethanol (Kelthane ®),
bis(pentochloro-2,4-cyclopentadien-lyl) (Pentac ®),
trichlohexyltin hydroxide (Plictran ®);

NEMATICIDES

2-[diethoxyphoxyphinylimino]-1,3-dithietane (Nematak ®), S-methyl 1-(dimethylcarbamoyl)-N-(methylcarbamoyloxy)-thioformimidate (Vydate ®),
S-methyl 1-carbamoyl-N-(methylcarbamoyloxy)thioformidate, N-isopropylphosphoramidic acid, O-ethyl-O'[4-(methylthio)-m-tolyl]diester (Nemacur ®),

INSECTICIDES 3-hydroxy-N-methylcrotonamide(dimethylphosphate)ester(Azodrin ®),
methylcarbamic acid, ester with 2,3-dihydro-2,2-dimethyl-7-benzofuranol (Furadan ®),
O-[2,4,5-trichloro-α-(chloromethyl)benzyl]phosphoric acid, O',O'-dimethyl ester (Gardona ®),
2-mercaptosuccinic acid, diethyl ester, S-ester with thionophosphoric acid, dimethyl ester (Malathion ®),
phosphorothioic acid, O,O-dimethyl, O-p-nitrophenyl ester (methyl parathion)
methylcarbamic acid, ester with α-naphthol (Sevin ®), methyl O-(methylcarbamoyl)thiolacetohydroxamate (methomyl)
N'-(4-chloro-o-tolyl)-N,N-dimethylformamidine (Galecron ®),
O,O-diethyl-O-(2-isopropyl-4-methyl-6-pyrimidylphosphorothioate (Diazinon ®),
octachlorocamphene (toxaphene) O-ethyl O-p-nitrophenyl phenylphosphonothioate (EPN) cyano(3-phenoxyphenyl)-methyl-4-chloro-α-(1-methylethyl)-benzeneacetate (Pydrin ®),
(3-phenoxyphenyl)methyl(+)-cis, trans-3-(2,2,-dichloroethenyl)-2,2-dimethylcyclopropanecarboxylate, (Ambush ®),
dimethyl N,N'-[thiobis[(n-methylimino)carbonyloxy]]-bis[ethanimidothioate] (Larvin ®),
O-ethyl-S-(p-chlorophenyl)ethylphosphonodithioate (Curacron ®),
phosphorothiolothionic acid, O-ethyl-O-[4-(methylthio)phenyl]-S-n-propyl ester (Bolstar ®).

Additional biological active agents which can be mixed with compounds of this invention of formula I include:
O,O-dimethyl O-(2,4,5-trichlorophenyl)phosphorothioate (Ronnel ®);
O,O-diethyl O-(3-chloro-4-methyl-2-oxo-2H-1-benzapyran-7-yl)phosphorothioate (Co-Ral ®);
Dimethyl 2,2-dichlorovinyl phosphate (Dichlorvos);
N-(mercaptomethyl)phthalimide S-(O,O-dimethyl phosphorodithioate (Imidan ®);
2,2-Bis(p-methoxyphenyl)-1,1,1-trichloroethane (Methoxychlor);
Octachloro-4,7-methanotetrahydroindane (Chlordane);
O,O-diethyl-O-(2-isopropyl-6-methyl-5-pyrimidinyl) phosphorothioate (Diazinon);
DL-2-allyl-4-hydroxy-3-methyl-2-cyclopenten-1-one ester of dicistranschrysanthemum monocarboxylic acid (Allethrin).

EXAMPLE 13

The foliage only of red kidney bean plants in the two-leaf stage is sprayed to run-off with dispersions of compounds of this invention at various concentrations. Dispersions are prepared by dissolving appropriately weighed quantities of the active ingredient in 10 ml of acetone and diluting to 100 ml of water containing surface active agent (Duponol ® L-144 WDG) at 1:3000. After drying, leaves are excised and placed in covered 10 cm petri dishes along with moist filter paper to keep them fresh. Ten southern armyworm larvae are placed in each dish. The units are kept in a room maintained at 25±2° C. 53±5% RH. Results are recorded at the end of two days.

| Compound | Concentration % | Mortality % |
|---|---|---|
| dimethyl N,N'-[2,3-butane-diylidenebis[nitrilooxy-carbonyl(N-methylimino)-thio(N-methylimino)carbonyloxy]]bis[ethanimidothioate] | .004 .002 | 95 90 |
| dimethyl N,N'-[1,2-propane-diylidenebis[nitrilooxy-carbonyl(N-methylimino)thio-(N-methylimino)carbonyloxy]]bis[ethanimidothioate] | .01 .005 .0025 | 100 100 95 |
| dimethyl N,N'-[2,4-pentane-diylidenebis[nitrilooxy-carbonyl(N-methylimino)thio-(N-methylimino)carbonyloxy]]bis[ethanimidothioate] | .01 .005 | 100 80 |
| dimethyl N,N'-[2,5-hexane-diylidenebis[nitrilooxy-carbonyl(N-methylimino)-thio(n-methylimino)carbonyloxy]]bis[ethanimidothioate] | .01 .005 | 100 90 |
| Untreated | — | 0 |

EXAMPLE 14

The foliage of red kidney bean plants in the two-leaf stage is sprayed to run-off with dispersions of compounds of this invention at various concentrations. Dispersions are prepared by dissolving appropriately weighed quantities of the active ingredient in 10 ml of acetone and diluting to 100 ml with water containing surface active (Duponol ® L-144 WDG) at 1:3000. After drying, plants are placed under artificial light in a room maintained at 25±2° C., 54±5% RH. After the designated period, leaves are excised and placed in covered 10 cm petri dishes along with moist filter paper to keep them fresh. Ten southern armyworm larvae are placed in each dish. The units are kept in a room maintained at 25±2° C., 54% RH. Results are recorded at the end of two days.

| Compound | Concentration % | Days 2 | (% Dead) 7 |
|---|---|---|---|
| dimethyl N,N'-[2,3-butane-diylidenebis[nitrilooxy-carbonyl(N-methylimino)-thio(N-methylimino)carbonyloxy]]bis[ethanimidothioate] | .01 .005 | 90 100 | 100 95 |
| Untreated Check | | 0 | 0 |

EXAMPLE 15

Potted cotton plants approximately 25 cm high having 3-4 true leaves are sprayed to run-off with aqueous dispersions of compounds of this invention at 500 ppm. The sprays contain surface active agent (Duponol® L-144 WDG) at a concentration of 1:3000. Another set of plants is similarly treated with methomyl. After drying, plants are set out in the greenhouse and held for obserations.

| Compound (500 ppm AI[1]) | Rating[2] (5 Days) |
| --- | --- |
| dimethyl N,N'-[2,3-butane-diylidenebis[nitrilooxy-carbonyl(N-methylimino)-thio(N-methylimino)carbonyl oxy]]bis[ethanimidothioate] | 0 |
| Methomyl | 4R |
| Untreated Control | 0 |

[1]AI = active ingredient
[2]"R" denotes typical methomyl effect, i.e., reddening of older leaves, slight puckering and black stippling of younger leaves. Rating is on the basis of 0 to 10 indicating total leaf area involvement.

EXAMPLE 16

Tobacco budworm (*Heliothis virescens*) larvae are treated topically with compounds of the invention. One microliter of each concentration used is applied to the dorso-thoracic area of each larva tested. The stock solutions are prepared by dissolving appropriately weighed quantities of active ingredient in predetermined quantities of acetone. Further dituting with acetone yields the desired concentrations. Larvae were treated in individual 1-oz. cups in which were reared on artificial diet. Fifteen or twenty larvae were treated with each desired concentration and kept in a room at 25±2° C. Results were recorded 2 days after treatment.

| Compound | Concentration (μg/larva) | % Mortality (48 hrs) |
| --- | --- | --- |
| dimethyl N,N'-[2,3-butane-diylidenebis[nitrilooxy-carbonyl(N-methylimino)-thio(N-methylimino)carbonyl-oxy]]bis[ethanimidothioate] | 0.25<br>0.125 | 93<br>85 |
| dimethyl N,N'-[2,4-pentane-diylidenebis[nitrilooxy-carbonyl(N-methylimino)thio-(N-methylimino)carbonyl-oxy]]bis[ethanimidothioate] | 0.5<br>0.25 | 87<br>73 |
| Untreated | — | 0 |

EXAMPLE 17

Dimethyl N,N'-[[1,2-ethanediylidenebis[nitrilooxycarbonyl(N-methylimino)thio(N-methylimino)carbonyloxy]]]-bis-[ethanimidothioate], was dissolved in acetone and mixed into soil containing the rootknot nematode, *Meloidogyne incognita*. Dimethyl N,N'-[[1,3-propanediylbis[nitrilooxycarbonyl (N-methylimino)thio(N-methylimino)carbonyloxy]]]bis-[ethanimidothioate], was similarly dissolved in acetone and mixed into soil containing the rootknow nematode, *Meloidogyne incognita*. The treated soil samples were planted with cucumber seeds. After two weeks, the roots were examined for nematode injury and the results are summarized below.

| Compound | kg/ha | % Nematode Control |
| --- | --- | --- |
| dimethyl N,N'-[2,3-butane-diylidenebis[nitrilooxy-carbonyl(N-methylimino)-thio(N-methylimino)carbonyl-oxy]]bis[ethanimidothioate] | 15 | 100 |
| Untreated Control | — | 0 |

EXAMPLE 18

Four-ounce wide mouth jars, each containing 10 black carpenter ants (*Camponotus pennsylvanicus*) were sprayed with 100 and 10 ppm concentration of the indicated compound in acetone solution. The ants were confined with caps which were also sprayed. Forty-eight hours later, percent mortality was determined.

| Compound | Spray Concentration ppm | % Mortality |
| --- | --- | --- |
| dimethyl N,N'-[2,3-butane-diylidenebis[nitrilooxy-carbonyl(N-methylimino)-thio(N-methylimino)-carbonyloxy]]bis[ethan-imidothioate] | 100<br>10 | 100<br>100 |

EXAMPLE 19

Four-ounce wide mouth jars, each containing 10 brown dog ticks (*Rhipicephalus sanguineus*) were sprayed with 10 and 5 ppm concentration of the indicated compound in acetone solution. The ticks were confined with caps which were also sprayed. Forty-eight hours later, percent mortality was determined.

| Compound | Spray Concentration ppm | % Mortality |
| --- | --- | --- |
| dimethyl N,N'-[2,3-butane-diylidenebis[nitrilooxy-carbonyl(N-methylimino)-thio(N-methylimino)-carbonyloxy]]bis[ethan-imidothioate] | 10<br>5 | 100<br>100 |

EXAMPLE 20

Uniform test units consisting of cut branches of wild cherry trees bearing four eastern tent caterpillar nests in can-type vases were prepared and sprayed with dispersions of this compound. They were kept out of doors and results were read 5 days after treatment.

Evaluation was made by counting all caterpillars inside and outside the nests.

| Compound | Concentration oz(ai)/100 gal | % Mortality |
| --- | --- | --- |
| dimethyl N,N'-[2,3-butane-diylidenebis[nitrilooxy-carbonyl(N-methylimino)-thio(N-methylimino)-carbonyloxy]]bis[ethan-imidothioate] | 1<br>0.25 | 99<br>99 |

What is claimed is:
1. A compound of the formula

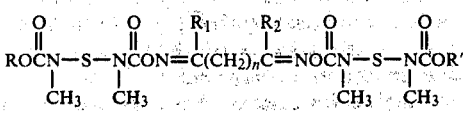

wherein
R and R' are independently

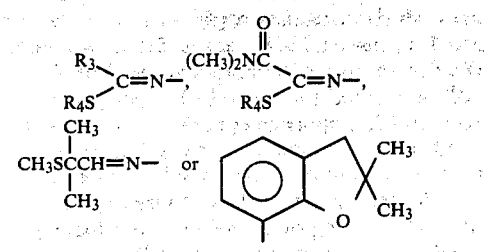

$R_1$ is hydrogen, $C_1-C_4$ alkyl, $C_5-C_6$ cycloalkyl, $C_1-C_3$ alkylthio, chlorine, chloromethyl,

phenyl or phenyl substituted with $C_1-C_4$ alkyl;
$R_2$ is hydrogen, $C_1-C_4$ alkyl, $C_5-C_6$ cycloalkyl, chlorine, $C_1-C_3$ alkylthio, phenyl or phenyl substituted with $C_1-C_4$ alkyl;
$R_1$ and $R_2$ can be taken together to form a carbocyclic bridge of three to five carbon atoms, or a bridge of the formula —$SCH_2CH_2S$—;
$R_3$ is $C_1-C_3$ alkyl;
$R_4$ is $C_1-C_3$ alkyl;
$R_5$ is $C_1-C_3$ alkyl;
$R_6$ is $C_1-C_6$ alkyl; and
n is 0, 1 or 2;
provided that n is 0 when
(1) $R_1$ is chloromethyl or $R_4SCH_2$, or
(2) $R_1$ and $R_2$ are taken together to form a carbocyclic bridge or a bridge of the formula —$SCH_2CH_2S$—, or
(3) at least one of $R_1$ and $R_2$ is alkylthio;
and provided that when n is 0,
one of $R_1$ and $R_2$ cannot be H when the other is phenyl or phenyl substituted with $C_1-C_4$ alkyl;
and further provided that when n is 1,
$R_1$ and $R_2$ cannot both be t-butyl, phenyl, phenyl substituted with $C_1-C_4$ alkyl or combination thereof.
2. A compound of claim 1 where R and R' are identical.
3. A compound of claim 1 where R and R' are identical and are

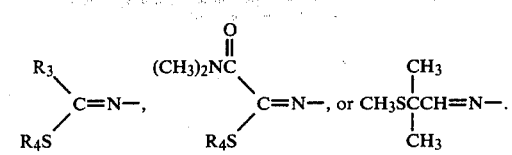

4. A compound of claim 1 where $R_3$ is $CH_3$.
5. A compound of claim 1 where $R_1$ and $R_2$ are independently hydrogen, $C_1-C_4$ alkyl,

phenyl, or phenyl substituted with $C_1-C_4$ alkyl or where $R_1$ and $R_2$ are taken together to form a carbocyclic bridge of three to five carbon atoms.
6. A compound of claim 1 where n is 0.
7. A compound of claim 1 where R and R' are identical, $R_3$ is $CH_3$, $R_1$ and $R_2$ are independently hydrogen, $C_1-C_4$ alkyl,

phenyl or phenyl substituted with $C_1-C_4$ alkyl or where $R_1$ and $R_2$ are taken together to form a carbocyclic bridge of three to five carbon atoms and n is 0.
8. A compound of claim 7 where $R_3$ is $CH_3$, $R_1$ and $R_2$ are independently hydrogen, $C_1-C_4$ alkyl,

phenyl or phenyl substituted with $C_1-C_4$ alkyl or where $R_1$ or $R_2$ are taken together to form a carbocyclic bridge of three to five carbon atoms and n is 0.
9. A compound of claim 7 where R and R' are

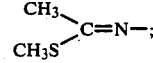

$R_1$ and $R_2$ ar independently hydrogen or $C_1-C_4$ alkyl; and n is 0; provided at least one of $R_1$ and $R_2$ is other than hydrogen.
10. The compound of claim 1 which is dimethyl, N,N'-[2,3-butanediylidenebis[nitrilooxycarbonyl-(N-methylimino)thio(N-methylimino)-carbonyloxy]]bis[ethanimidothioate].
11. The compound of claim 1 which is dimethyl N,N'-[1,2-propanediylidenebis[nitrilooxycarbonyl-(N-methylimino)thio(N-methylimino)-carbonyloxy]]bis[ethanimidothioate].
12. The compound of claim 1 which is dimethyl N,N'-[2,4-pentanediylidenebis[nitrilooxycarbonyl (N-methylimino)thio(N-methylimino)-carbonyloxy]]bis[ethanimidothioate].
13. The compound of claim 1 which is dimethyl N,N'-[2,5-hexanediylidenebis[nitrilooxycarbonyl-(N-methylimino)thio(N-methylimino)-carbonyloxy]]bis[ethanimidothioate].
14. The compound of claim 1 which is N-methyl-N-[N-methyl-N-(2-methyl-2-methylthio-propylideneaminooxycarbonyl)aminothio]carbamic acid, diester with 2,3-butanedione, dioxime.
15. The compound of claim 1 which is N,N'-[2,3-butanediylidenebis[nitrilooxycarbonyl-(N-methylaminothio-(N-methylimino)carbonyloxy]bis]-2-(dimethylamino)-2-oxoethanimidothioic acid, dimethyl ester.
16. An agricultural composition consisting essentially of a diluent, surfactant or mixture thereof and an insecticidally, acaricidally, or nematicidally effective amount of a compound of claim 1.

17. An agricultural composition consisting essentially of a diluent, surfactant or mixture thereof and an insecticidally, acaricidally, or nematicidally effective amount of a compound of claim 2.

18. An agricultural composition consisting essentially of a diluent, surfactant or mixture thereof and an insecticidally, acaricidally, or nematicidally effective amount of a compound of claim 3.

19. An agricultural composition consisting essentially of a diluent, surfactant or mixture thereof and an insecticidally, acaricidally, or nematicidally effective amount of a compound of claim 4.

20. An agricultural composition consisting essentially of a diluent, surfactant or mixture thereof and an insecticidally, acaricidally, or nematicidally effective amount of a compound of claim 5.

21. An agricultural composition consisting essentially of a diluent, surfactant or mixture thereof and an insecticidally, acaricidally, or nematicidally effective amount of a compound of claim 6.

22. An agricultural composition consisting essentially of a diluent, surfactant or mixture thereof and an insecticidally, acaricidally, or nematicidally effective amount of a compound of claim 7.

23. An agricultural composition consisting essentially of a diluent, surfactant or mixture thereof and an insecticidally, acaricidally, or nematicidally effective amount of a compound of claim 8.

24. An agricultural composition consisting essentially of a diluent, surfactant or mixture thereof and an insecticidally, acaricidally, or nematicidally effective amount of a compound of claim 9.

25. An agricultural composition consisting essentially of a diluent, surfactant or mixture thereof and an insecticidally, acaricidally, or nematicidally effective amount of the compound of claim 10.

26. An agricultural composition consisting essentially of a diluent, surfactant or mixture thereof and an insecticidally, acaricidally, or nematicidally effective amount of the compound of claim 11.

27. An agricultural composition consisting essentially of a diluent, surfactant or mixture thereof and an insecticidally, acaricidally, or nematicidally effective amount of the compound of claim 12.

28. An agricultural composition consisting essentially of a diluent, surfactant or mixture thereof and an insecticidally, acaricidally, or nematicidally effective amount of the compound of claim 13.

29. An agricultural composition consisting essentially of a diluent, surfactant or mixture thereof essentially of a diluent, surfactant or mixture thereof and an insecticidally, acaricidally, or nematicidally effective amount of the compound of claim 14.

30. An agricultural composition consisting essentially of a diluent, surfactant or mixture thereof and an insecticidally, acaricidally, or nematicidally effective amount of the compound of claim 15.

31. A method for control of insects, acari, or nematodes which comprises applying to a locus to be protected an insecticidally, acaricidally, or nematicidally effective amount of a compound of claim 1.

32. A method for control of insects, acari, or nematodes which comprises applying to a locus to be protected an insecticidally, acaricidally, or nematicidally effective amount of a compound of claim 2.

33. A method for control of insects, acari, or nematodes which comprises applying to a locus to be protected an insecticidally, acaricidally, or nematicidally effective amount of a compound of claim 3.

34. A method for control of insects, acari, or nematodes which comprises applying to a locus to be protected an insecticidally, acaricidally, or nematicidally effective amount of a compound of claim 4.

35. A method for control of insects, acari, or nematodes which comprises applying to a locus to be protected an insecticidally, acaricidally, or nematicidally effective amount of a compound of claim 5.

36. A method for control of insects, acari, or nematodes which comprises applying to a locus to be protected an insecticidally, acaricidally, or nematicidally effective amount of a compound of claim 6.

37. A method for control of insects, acari, or nematodes which comprises applying to a locus to be protected an insecticidally, acaricidally, or nematicidally effective amount of a compound of claim 7.

38. A method for control of insects, acari, or nematodes which comprises applying to a locus to be protected an insecticidally, acaricidally, or nematicidally effective amount of a compound of claim 8.

39. A method for control of insects, acari, or nematodes which comprises applying to a locus to be protected an insecticidally, acaricidally, or nematicidally effective amount of a compound of claim 9.

40. A method for control of insects, acari, or nematodes which comprises applying to a locus to be protected an insecticidally, acaricidally, or nematicidally effective amount of the compound of claim 10.

41. A method for control of insects, acari, or nematodes which comprises applying to a locus to be protected an insecticidally, acaricidally, or nematicidally effective amount of the compound of claim 11.

42. A method for control of insects, acari, or nematodes which comprises applying to a locus to be protected an insecticidally, acaricidally, or nematicidially effective amount of the compound of claim 12.

43. A method for control of insects, acari, or nematodes which comprises applying to a locus to be protected an insecticidally, acaricidally, or nematicidally effective amount of the compound of claim 13.

44. A method for control of insects, acari, or nematodes which comprises applying to a locus to be protected an insecticidally, acaricidally, or nematicidally effective amount of the compound of claim 14.

45. A method for control of insects, acari, or nematodes which comprises applying to a locus to be protected an insecticidally, acaricidally, or nematicidally effective amount of the compound of claim 15.

* * * * *